United States Patent [19]

Yamatsu et al.

[11] Patent Number: 4,571,408

[45] Date of Patent: Feb. 18, 1986

[54] α,β-DIHYDROPOLYPRENYL DERIVATIVES FOR TREATING HEPATITIS

[75] Inventors: Isao Yamatsu, Kawaguchi; Yuichi Inai, Tokyo; Shinya Abe, Nakamura; Hideaki Watanabe, Aichi; Toshiji Igarashi, Tokorozawa; Hiroyuki Shiojiri, Sayama; Yoshio Tanabe, Saitama; Kuniko Hara, Tokyo, all of Japan

[73] Assignee: Eisai Co., Ltd., Tokyo, Japan

[21] Appl. No.: 543,748

[22] Filed: Oct. 20, 1983

Related U.S. Application Data

[62] Division of Ser. No. 269,930, May 28, 1981, Pat. No. 4,481,217.

[30] Foreign Application Priority Data

May 30, 1980 [JP]  Japan .................................. 55-71488
May 30, 1980 [JP]  Japan .................................. 55-71489

[51] Int. Cl.$^4$ ...................... C07C 57/03; A61K 31/22; A61K 31/23
[52] U.S. Cl. ............................ 514/546; 260/410.9 R; 260/413; 514/549; 514/724; 514/894; 560/261; 568/879
[58] Field of Search ............... 260/410.9 R, 410.9 M, 260/413 L; 560/261; 568/879; 424/311, 312, 314, 318, 343; 514/549, 894, 546, 724

[56] References Cited

U.S. PATENT DOCUMENTS

| | | | |
|---|---|---|---|
| 3,712,922 | 1/1973 | Henrick et al. | 260/413 L X |
| 4,107,193 | 8/1978 | Kijima et al. | 260/413 L X |
| 4,116,955 | 9/1978 | Ichikawa et al. | 260/404 X |
| 4,199,519 | 4/1980 | Mishima et al. | 260/413 L |
| 4,260,551 | 4/1981 | Mishima et al. | 560/224 X |
| 4,293,500 | 10/1981 | Morel | 260/410.9 R |

OTHER PUBLICATIONS

Wagner & Zook, *Synthetic Organic Chemistry*, pp. 155, 230, 412 and 480, John Wiley & Sons, 1953.

*Primary Examiner*—Thomas A. Waltz
*Attorney, Agent, or Firm*—Flynn, Thiel, Boutell & Tanis

[57] ABSTRACT

An α,β-dihydropolyprenyl derivative having the formula (I):

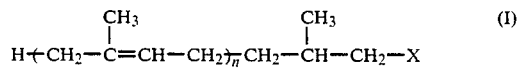

wherein X represents a group of —COOR$_1$ or —CH$_2$OR$_2$ in which R$_1$ is the hydrogen atom or an alkyl group having one to four carbon atoms and R$_2$ is the hydrogen atom or an aliphatic acyl group having one to four carbon atoms; and n is an integer of one to four. A process for the preparation of the α,β-dihydropolyprenyl derivative and a therapeutic agent for treatment of liver diseases comprising the same are also disclosed.

14 Claims, No Drawings

α,β-DIHYDROPOLYPRENYL DERIVATIVES FOR TREATING HEPATITIS

This is a division of application Ser. No. 269,930, filed May 28, 1981, now U.S. Pat. No. 4,481,217, issued Nov. 6, 1984.

This invention relates to α,β-dihydropolyprenyl derivatives having the formula (I):

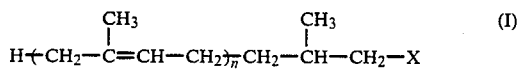

wherein X represents a —COOR$_1$ group or a —CH$_2$OR$_2$ group, in which R$_1$ is hydrogen or a lower alkyl group and R$_2$ is hydrogen or an aliphatic acyl group having one to four carbon atoms; and n is an integer of one to four. The invention further relates to processes for the preparation of compounds of formula (I) and therapeutic compositions for treatment of liver diseases comprising compounds of formula (I).

More particularly, this invention relates to α,β-dihydropolyprenylcarboxylic acids and derivatives thereof having the formula (I) in which X represents —COOR$_1$ group, that is, compounds having the following formula (II):

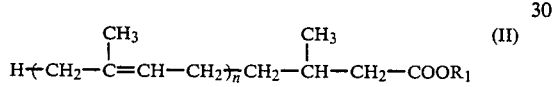

in which R$_1$ and n have the same meanings as set forth above, and further relates to α,β-dihydropolyprenyl alcohols and derivatives thereof having the formula (I) in which X represents a —CH$_2$OR$_2$ group, that is, compounds having the following formula (III):

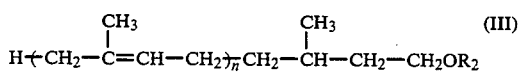

in which R$_2$ and n have the same meanings as set forth above.

In the above-mentioned formulae, R$_1$ can be an alkyl having 1 to 6, preferably 1 to 4, carbon atoms, such as methyl, ethyl, i-propyl, n-propyl, t-butyl, n-butyl, n-pentyl and n-hexyl and R$_2$ can be acetyl, propionyl, butyryl or isobutyryl.

The α,β-dihydropolyprenylcarboxylic acids and derivatives thereof having the formula (II) can be prepared by the following reaction steps:

(a) a compound having the formula (VII):

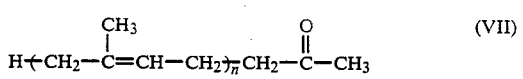

in which n is a integer of one to four, and a compound having the formula (VIII):

in which R$_5$ represents a lower alkyl group are reacted to obtain a compound having the formula (IX):

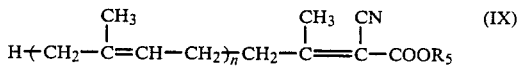

in which n and R$_5$ have the same meanings as set forth above;

(b) the compound of the formula (IX) is then reduced to obtain a compound having the formula (X):

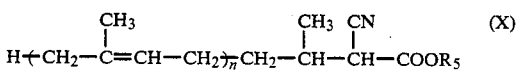

in which n and R$_5$ have the same meanings as set forth above; (c) the compound of the formula (X) is subjected to a decarboxylation reaction in the presence of a base to obtain a compound having the formula (IV):

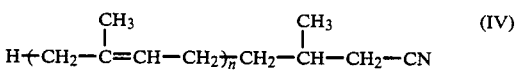

in which n has the same meaning as set forth above;

(d) the compound of the formula (IV) is hydrolyzed in the presence of a base to obtain a compound having the formula (II-1):

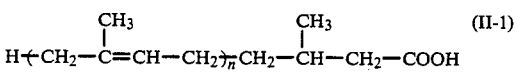

in which n has the same meaning as set forth above; and if a derivative of the compound of formula (II-1) is desired, (e) the compound of the formula (II-1) or a reactive derivative thereof is reacted with a compound having the formula (V):

$$R_3—OH \quad (V)$$

in which R$_3$ represents an alkyl group having one to four carbon atoms, to obtain a compound having the formula (II-2):

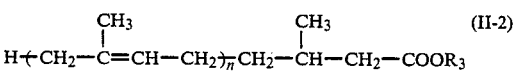

in which n and R$_3$ have the same meanings as set forth above.

The reaction between the compound of the formula (VII) and the compound of the formula (VIII) in the (a) step can be carried out in the presence of a base or an acid, such as ammonium acetate—acetic acid, piperidine or morpholine.

The reduction reaction in the (b) step can be carried out using a reducing agent such as sodium borohydride.

Examples of the bases to be employed in the (c) and (d) steps include potassium hydroxide, sodium hydroxide and pyridine—copper.

The reaction in the (e) step can be carried out by a conventional esterification method. For instance, the carboxylic acid of the formula (II-1) can be converted into its ester form by the reaction in the presence of a condensing agent, such as p-toluenesulfonyl chloride, dicyclohexylcarbodiimide, ethyl polyphosphate, ethyl chlorocarbonate, oxalyl chloride or trifluoroacetic acid.

The reaction in the (e) step can be carried out using a reactive derivative of the carboxylic acid of the formula (II-1). Examples of the reactive derivatives include the corresponding acid chloride and the corresponding acid anhydride.

The α,β-dihydropolyprenyl alcohol and derivatives thereof having the formula (III) can be prepared by the following reaction steps:

(f) the compound having the above-mentioned formula (II-1) is reduced in the presence of a reducing agent to obtain a compound having the formula (III-1):

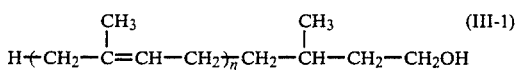

in which n is an integer of one to four;

and if a derivative of the compound of formula (III-1) is desired, (g) the compound of the formula (III-1) is reacted with a compound having the formula (VI):

in which $R_4$ represents an aliphatic acyl group having one to four carbon atoms or a reactive derivative thereof, to obtain a compound having the formula (III-2):

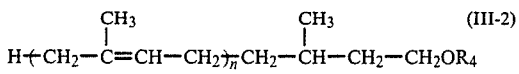

in which n and $R_4$ have the same meanings as set forth above.

The reduction reaction in the (f) step can be carried out in an ether solvent, such as diethyl ether or tetrahydrofuran, and in the presence of a reducing agent, such as lithium aluminum hydride.

The reaction in the (g) step can be carried out by a conventional esterification method. For instance, the compound of the formula (III-1) can be subjected to esterification in the form of its reactive derivative, such as the corresponding acid chloride or the corresponding acid anhydride. If the compound of the formula (III-1) is employed per se for the esterification reaction, the reaction can be carried out in the presence of a condensing agent, such as p-toluenesulfonyl chloride, dicyclohexylcarbodiimide, ethyl polyphosphate, ethyl chlorocarbonate, oxalyl chloride or trifluoroacetic acid.

The α,β-dihydropolyprenyl derivatives of the formula (I) according to this invention are of value as a therapeutic agent for the treatment of liver diseases. The liver possibly suffers from various diseases, such as inflammation, degeneration, necrosis, failure of the function for secretion of biliary products and abnormal carbohydrate metabolism, due to a variety of causes, such as excessive drinking or alcoholic drinks, malnutrition, viruses, chemical substances and toxic materials. The α,β-dihydropolyprenyl derivatives of the formula (I) are effective for treating these liver diseases or for preventing these liver diseases.

The α,β-dihydropolyprenyl derivatives of the formula (I), according to the invention, can be administered orally or parenterally to human beings. Oral administration is particularly preferred. The dosage generally ranges from 50 to 2,000 mg per day for an adult, and more preferably, a dosage ranging from 200 to 600 mg./day for an adult human being is employed. The compound of the formula (I) can be administered in a variety of forms, such as granules, powders, hard capsules, tablets and soft capsules. These forms are conventionally employed in pharmaceutical preparations and they can be prepared in the conventional manners.

The present invention will be further described by reference to the following examples relating to pharmacological activity and preparation of compounds. However, these examples do not restrict the scope of the invention.

PHARMACOLOGICAL TESTS

Compounds for testing (A) (E, E)-3,7,11,15-tetramethyl-6,10,14-hexadecatrienoic acid (B) ethyl (E, E)-3,7,11,15-tetramethyl-6,10,14-hexadecatrienoate (C) (E, E)-3,7,11,15-tetramethyl-6,10,14-hexadecatrien-1-ol (D) (E, E)-3,7,11,15-tetramethyl-6,10,14-hexadecatrienyl acetate

Test method

Activity against liver disease (hepatitis) induced by D-galactosamine

D-Galactosamine hydrochloride and the above-listed compound were administered (1) subcutaneously in the dosage of 200 mg./kg. each time and (2) orally in the dosage of 400 mg./kg. each time, respectively, to rats (SD strain, weight: approximately 250 g.) according to the schedule described hereinafter. After completion of the administrations, the blood was collected from the rats and there were measured the GOT value, GPT value and alkali phosphotase value, all of which are indicative of the degree of liver disease.

Each test compound was administered in the form of a suspension thereof in a 5% aqueous gum arabic solution. The D-galactosamine hydrochloride was administered in the form of an aqueous solution thereof in distilled water adjusted to pH 7 by addition of potassium hydroxide.

There were provided the test compound groups (nine rats per each group) in which the rats were administered with the test compound and with D-galactosamine hydrochloride; a control group (fourteen rats) in which the rats were administered with a plain 5% aqueous gum arabic solution free of the test compound and with D-galactosamine hydrochloride; and a normal group (eight rats) in which the rats were not administered with either the test compound or D-galactosamine hydrochloride.

Administration schedule

| Hour | Adminstration |
| --- | --- |
| 0 (start) | test compound |
| 4 | test compound and D-galactosamine hydrochloride |
| 10 | test compound and D-galactosamine hydrochloride |
| 24 | test compound and D-galactosamine hydrochloride |
| 28 | blood collection |

Test results

The results are set forth in Table 1.

TABLE 1

| Test group | Subject for testing | | |
|---|---|---|---|
| | GPT value (carmen unit) | GOT value (carmen unit) | Alkali phosphotase value (KA - u) |
| Normal group | 34.8 ± 1.9 | 129.4 ± 12.6 | 49.3 ± 4.4 |
| Control group | 395.7 ± 49.3 | 573.7 ± 59.1 | 67.4 ± 2.9 |
| Test compound group | | | |
| Compound A | 208.3 ± 30.7 | 312.4 ± 39.5 | 56.2 ± 4.1 |
| Compound B | 199.7 ± 28.9 | 307.1 ± 40.1 | 55.8 ± 3.8 |
| Compound C | 185.6 ± 41.4 | 337.7 ± 45.1 | 54.2 ± 6.1 |
| Compound D | 178.7 ± 46.9 | 315.3 ± 50.6 | 53.5 ± 5.8 |

Toxicity

Each of the above-listed compounds, A, B, C and D was suspended in a 5% aqueous gum arabic solution and then was administered orally to ten rats (Wistar strain) in the dosage of 4,000 mg./kg. No deaths of the rats were observed.

EXAMPLE 1

(E, E)-3,7,11,15-Tetramethyl-6,10,14-hexadecatrienoic acid (a) Ethyl (E, E)-2-cyano-3,7,11,15-tetramethyl-6,10,14-hexadecatrienoate In 200 ml. of benzene was dissolved 50 g. of farnesyl acetone, and then 28 g. of ethyl cyanoacetate, 5 g. of ammonium acetate and 5 g. of acetic acid were added to the solution. The mixture was then refluxed for 8 hours with removal of the produced water. The reaction mixture then was washed with water and dried. To this mixture there was added dropwise a solution of 4.3 g. of sodium borohydride in 50 ml. of ethanol, under stirring and at 10°-20° C. The stirring was continued for 1 hour. Then, 50 ml. of 10% acetic acid was added to the reaction mixture, and the mixture was subsequently washed with water and dried. The solvent was removed by evaporation and then the residue was purified by silica gel column chromatography to obtain 50.5 g. of the desired oily product.

(b) (E, E)-3,7,11,15-Tetramethyl-6,10,14-hexadecatrienonitrile

To the entirety of the product obtained in the above (a) step, there were added 29 g. of sodium hydroxide and 100 ml. of propylene glycol, and the mixture was stirred at room temperature for 10 min. The reaction mixture was made acidic by addition of 6N hydrochloric acid, and was then extracted with benzene. The extract was then washed with water and dried. The solvent was then removed by evaporation. The obtained oily product was dissolved in 100 ml. of pyrydine, and the resulting solution was refluxed for 2 hours after addition of 0.5 g. of copper powder. Subsequently, the copper powder was removed by filtration and the solvent was removed by evaporation. The residue was dissolved in n-hexane, washed with water and dried. The solvent was then removed by evaporation and the residue was purified by silica gel column chromatography to obtain 34 g. of the desired oily product.

(c) (E, E)-3,7,11,15-Tetramethyl-6,10,14-hexadecatrienoic acid

To 34 g. of the product obtained in the above (b) step, there were added 23 g. of potassium hydroxide, 10 ml. of water and 70 ml. of propylene glycol, and the mixture was stirred at 130° C. for 7 hours. The reaction mixture was made acidic by addition of hydrochloric acid, and was then extracted with n-hexane. The extract was washed with water and dried, and the solvent was removed by evaporation. The residue was purified by silica gel column chromatography to obtain 30 g. of the desired oily product.

Infrared Absorption Spectrum (cm$^{-1}$, neat): 3,600-2,400, 1,710.

Mass Spectrum: 306 (M+).

Elementary Analysis (calculated for $C_{20}H_{34}O_2$):

| | C | H |
|---|---|---|
| Calculated (%) | 78.38 | 11.18 |
| Found (%) | 78.21 | 11.02 |

NMR Spectrum (δ, CDCl$_3$): 0.99 (3H, s), 1.2-1.5 (3H, m), 1.6 (9H, s), 1.72 (3H, s), 1.9-2.2 (10H, m), 2.20 (2H, d), 5.0-5.2 (3H, m), 11.3 (1H, br).

EXAMPLE 2

Ethyl (E, E)-3,7,11,15-tetramethyl-6,10,14-hexadecatrienoate

In 50 ml. of anhydrous tetrahydrofuran was dissolved 9.2 g. of the product obtained in the (c) step of Example 1. To the resulting solution were added successively 3 g. of triethylamine and 3.3 g. of ethyl chlorocarbonate at 0° C., and the mixture was then stirred for 20 min. The reaction mixture was, after addition of 50 ml. of ethanol, refluxed for 2 hours, and the solvent was then removed by evaporation. The residue was extracted with 100 ml of n-hexane, and the extract was washed with water and dried. The solvent was removed by evaporation, and the residual oil was purified by silica gel column chromatography to obtain 8 g. of the desired oily product.

Infrared Absorption Spectrum (cm$^{-1}$, neat): 1,735, 1,300, 1,050.

Mass Spectrum: 334 (M+).

Elementary Analysis (calculated for $C_{22}H_{38}O_2$):

| | C | H |
|---|---|---|
| Calculated (%) | 78.98 | 11.45 |
| Found (%) | 79.10 | 11.58 |

NMR spectrum (δ, CDCl$_3$): 0.99 (3H, s), 1.2-1.5 (3H, m), 1.3 (3H, t), 1.6 (9H, s), 1.72 (3H, s), 1.9-2.2 (10H, m), 2.20 (2H, d), 4.2 (2H, q), 5.0-5.2 (3H, m).

EXAMPLE 3

(E)-3,7,11-Trimethyl-6,10-dodecadienoic acid (a) Ethyl (E)-2-cyano-3,7,11-trimethyl-6,10-dodecadienoate In 200 ml. of benzene was dissolved 50 g. of geranyl acetone, and then 42 g. of ethyl cyanoacetate, 6 g. of ammonium acetate and 6 g. of acetic acid were added to the solution. The mixture was then refluxed for 8 hours while removing the produced water. The reaction mixture was washed with water and dried. To this was added dropwise a solution of 5.7 g. of sodium borohydride in 40 ml. of ethanol, under stirring and at 10°-20° C. The stirring was continued for 1 hour. Then, 60 ml. of 10% acetic acid was added to the reaction mixture, and the mixture was subsequently washed with water and dried. The solvent was then removed by evaporation and the residue was purified by silica gel column chromatography to obtain 59 g. of the desired oily product.

(b) (E)-3,7,11-Trimethyl-6,10-dodecadienonitrile

To the entirety of the product obtained in the above (a) step, there were added 39 g. of sodium hydroxide and 120 ml. of propylene glycol, and the mixture was stirred at room temperature for 10 min. The reaction mixture was then made acidic by addition of 6N hydrochloric acid, and was then extracted with benzene. The extract was then washed with water and dried. The solvent was then removed by evaporation. The residue was dissolved in 120 ml. of pyridine, and the resulting solution was refluxed for 2 hours after addition of 0.6 g. of copper powder. Subsequently, the copper powder was removed by filtration and the solvent was removed by evaporation. The residue was dissolved in n-hexane, washed with water and dried. The solvent was then removed by evaporation, and the residue was purified by silica gel column chromatography to obtain 45 g. of the desired oily product.

(c) (E)-3,7,11-Trimethyl-6,10-dodecadienoic acid

To 40 g. of the product obtained in the above (b) step, there were added 35 g. of potassium hydroxide, 15 ml. of water and 80 ml. of propylene glycol, and the mixture was stirred at 130° C. for 7 hours. The reaction mixture was then made acidic by addition of hydrochloric acid, and was then extracted with n-hexane. The extract was washed with water and dried, and the solvent was removed by evaporation. The residue was purified by silica gel column chromatography to obtain 36 g. of the desired oily product.

Infrared Absorption Spectrum (cm$^{-1}$, neat): 3,600–2,400, 1,710.

Mass Spectrum: 238 (M$^+$).

Elementary Analysis (calculated for $C_{15}H_{26}O_2$):

|  | C | H |
|---|---|---|
| Calculated (%) | 75.58 | 11.00 |
| Found (%) | 75.44 | 10.91 |

NMR Spectrum (δ, CDCl$_3$): 0.99 (3H, s), 1.2–1.5 (3H, m), 1.6 (6H, s), 1.72 (3H, s), 1.9–2.2 (6H, m), 2.20 (2H, d), 5.0–5.2 (2H, m), 11.3 L (1H, br).

EXAMPLES 4–16

In Examples 4 through 16, a variety of compounds according to the invention were prepared in the same manner as described in Examples 1 through 3. The compounds and the resulting data are set forth in Table 2.

TABLE 2

$$H\!\!-\!\!(CH_2\!\!-\!\!\underset{\underset{CH_3}{|}}{C}\!\!=\!\!CH\!\!-\!\!CH_2)_{\overline{n}}\,CH_2\!\!-\!\!\underset{\underset{CH_3}{|}}{CH}\!\!-\!\!CH_2\!\!-\!\!COOR_1 \quad (II)$$

| Ex | n | R$_1$ | Molecular Formula Property | Analysis: Calculated (%) / Found (%) C | H | Mass Spectrum (M$^+$) | NMR Spectrum (δ, CDCl$_3$) |
|---|---|---|---|---|---|---|---|
| 4 | 1 | H | C$_{10}$H$_{18}$O$_2$ Oil | 70.54 / 70.41 | 10.66 / 10.48 | 170 | 0.99 (3H, s), 1.2~1.5 (3H, m), 1.6 (3H, s), 1.72 (3H, s), 1.9~2.2 (2H, m), 2.20 (2H, d), 5.0~5.2 (1H, m), 11.3 (1H, br) |
| 5 | 1 | —CH$_3$ | C$_{11}$H$_{20}$O$_2$ Oil | 71.69 / 71.54 | 10.94 / 10.78 | 184 | 0.99 (3H, s), 1.2~1.5 (3H, m), 1.6 (3H, s), 1.72 (3H, s), 1.9~2.2 (2H, m), 2.20 (2H, d), 3.7 (3H, s), 5.0~5.2 (1H, m) |
| 6 | 1 | —CH$_2$CH$_3$ | C$_{12}$H$_{22}$O$_2$ Oil | 72.68 / 72.77 | 11.18 / 11.11 | 198 | 0.99 (3H, s), 1.2~1.5 (3H, m), 1.3 (3H, t), 1.6 (3H, s), 1.72 (3H, s), 1.9~2.2 (2H, m), 2.20 (2H, d), 4.2 (2H, q), 5.0~5.2 (1H, m) |
| 7 | 1 | —CH$_2$CH$_2$CH$_3$ | C$_{13}$H$_{24}$O$_2$ Oil | 73.53 / 73.70 | 11.39 / 11.42 | 212 | 0.99 (3H, s), 1.0~1.3 (5H, m), 1.2~1.5 (3H, m), 1.6 (3H, s), 1.72 (3H, s), 1.9~2.2 (2H, m), 2.20 (2H, d), 4.2 (2H, q), 5.0~5.2 (1H, m) |
| 8 | 2 | —CH$_3$ | C$_{16}$H$_{28}$O$_2$ Oil | 76.14 / 76.27 | 11.18 / 11.05 | 252 | 0.99 (3H, s), 1.2~1.5 (3H, m), 1.6 (6H, s), 1.72 (3H, s), 1.9~2.2 (6H, m), 2.20 (2H, d), 3.7 (3H, s), 5.0~5.2 (2H, m) |
| 9 | 2 | —CH$_2$CH$_3$ | C$_{17}$H$_{30}$O$_2$ Oil | 76.64 / 76.76 | 11.35 / 11.24 | 266 | 0.99 (3H, s), 1.2~1.5 (3H, m), 1.3 (3H, t), 1.6 (6H, s), 1.72 (3H, s), 1.9~2.2 (6H, m), 2.20 (2H, d), 4.2 (2H, q), 5.0~5.2 (2H, m) |
| 10 | 2 | —CH$_2$CH$_2$CH$_3$ | C$_{18}$H$_{32}$O$_2$ Oil | 77.09 / 77.02 | 11.50 / 11.41 | 280 | 0.99 (3H, s), 1.0~1.3 (5H, m), 1.2~1.5 (3H, m), 1.6 (6H, s), 1.72 (3H, s), 1.9~2.2 (6H, m), 2.20 (2H, d), 4.2 (2H, q), 5.0~5.2 (2H, m) |
| 11 | 3 | —CH$_3$ | C$_{21}$H$_{36}$O$_2$ Oil | 78.69 / 78.77 | 11.32 / 11.46 | 320 | 0.99 (3H, s), 1.2~1.5 (3H, m), 1.6 (9H, s), 1.72 (3H, s), 1.9~2.2 (10H, m), 2.20 (2H, d), 3.7 (3H, s), 5.0~5.2 (3H, m) |

TABLE 2-continued $$H\text{-}(CH_2\text{-}\underset{\underset{CH_3}{|}}{C}=CH\text{-}CH_2)_n CH_2\text{-}\underset{\underset{CH_3}{|}}{CH}\text{-}CH_2\text{-}COOR_1 \quad (II)$$

| Ex | n | $R_1$ | Molecular Formula Property | Analysis: Calculated (%) / Found (%) C | H | Mass Spectrum ($M^+$) | NMR Spectrum ($\delta$, CDCl$_3$) |
|---|---|---|---|---|---|---|---|
| 12 | 3 | —CH$_2$CH$_2$CH$_3$ | C$_{23}$H$_{40}$O$_2$ Oil | 79.25 / 79.51 | 11.57 / 11.64 | 348 | 0.99 (3H, s), 1.0~1.3 (5H, m), 1.2~1.5 (3H, m), 1.6 (9H, s), 1.72 (3H, s), 1.9~2.2 (10H, m), 2.20 (2H, d), 4.2 (2H, q), 5.0~5.2 (3H, m) |
| 13 | 4 | H | C$_{25}$H$_{42}$O$_2$ Oil | 80.15 / 80.02 | 11.30 / 11.18 | 374 | 0.99 (3H, s), 1.2~1.5 (3H, m), 1.6 (12H, s), 1.72 (3H, s), 1.9~2.2 (14H, m), 2.20 (2H, d), 5.0~5.2 (1H, m), 11.3 (1H, br) |
| 14 | 4 | —CH$_3$ | C$_{26}$H$_{44}$O$_2$ Oil | 80.35 / 80.21 | 11.41 / 11.29 | 388 | 0.99 (3H, s), 1.2~1.5 (3H, m), 1.6 (12H, s), 1.72 (3H, s), 1.9~2.2 (14H, m), 2.20 (2H, d), 3.7 (3H, s), 5.0~5.2 (4H, m) |
| 15 | 4 | —CH$_2$CH$_3$ | C$_{27}$H$_{46}$O$_2$ Oil | 80.54 / 80.41 | 11.52 / 11.43 | 402 | 0.99 (3H, s), 1.2~1.5 (3H, m), 1.3 (3H, q), 1.6 (12H, s), 1.72 (3H, s), 1.9~2.2 (14H, m), 2.20 (2H, d), 4.2 (2H, q), 5.0~5.2 (4H, m) |
| 16 | 4 | —CH$_2$CH$_2$CH$_3$ | C$_{28}$H$_{48}$O$_2$ Oil | 80.71 / 80.88 | 11.61 / 11.76 | 416 | 0.99 (3H, s), 1.0~1.3 (5H, m), 1.2~1.5 (3H, m), 1.6 (12H, s), 1.72 (3H, s), 1.9~2.2 (14H, m), 2.20 (2H, d), 4.2 (2H, q), 5.0~5.2 (4H, m) |

EXAMPLE 17

(E, E)-3,7,11,15-Tetramethyl-6,10,14-hexadecatrien-1-ol

To 150 ml. of anhydrous diethyl ether there was added 1.9 g. of lithium aluminum hydride. To the mixture was dropwise added, under stirring and at 10° C., 1.53 g. of the carboxylic acid compound obtained in Example 1. The resulting mixture was then stirred at room temperature for 1 hour, and 1 ml. of ethyl acetate and 1 ml. of water were then added thereto. The mixture was subsequently washed with water and dried. The solvent was removed by evaporation and the resulting residual oil was purified by silica gel column chromatography to obtain 13.8 g. of the desired oily product.

Infrared Absorption Spectrum (cm$^{-1}$, neat): 3,640.
Mass Spectrum: 292 ($M^+$).
Elementary Analysis (calculated for C$_{20}$H$_{36}$O):

| | C | H |
|---|---|---|
| Calculated (%) | 82.12 | 12.40 |
| Found (%) | 82.03 | 12.31 |

NMR Spectrum ($\delta$, CDCl$_3$): 0.99 (3H, d), 1.2–1.5 (5H, m), 1.6 (9H, s), 1.72 (3H, s), 1.9–2.2 (11H, m), 3.6 (2H, t), 5.0–5.2 (3H, m).

EXAMPLE 18

(E, E)-3,7,11,15-Tetramethyl-6,10,14-hexadecatrienyl acetate

In 10 ml. of pyridine was dissolved 2.9 g. of the product obtained in Example 17, and to the solution was added 1.1 g. of acetic anhydride under stirring. The resulting mixture was then refluxed for 1 hour. The reaction mixture was then poured into 50 ml. of water, and was then extracted with n-hexane. The extract was washed with water and dried. The solvent was removed by evaporation. The residual oily product was purified by silica gel column chromatography to obtain 3.1 g. of the desired oily product.

Infrared Absorption Spectrum (cm$^{-1}$, neat): 1,735, 1,300, 1,050.
Mass Spectrum: 334 ($M^+$).
Elementary Analysis (calculated for C$_{22}$H$_{28}$O$_2$):

| | C | H |
|---|---|---|
| Calculated (%) | 78.98 | 11.45 |
| Found (%) | 78.82 | 11.41 |

NMR Spectrum ($\delta$, CDCl$_3$): 0.99 (3H, d), 1.2–1.5 (5H, m), 1.6 (9H, s), 1.72 (3H, s), 1.9–2.2 (11H, m), 2.0 (3H, s), 4.2 (2H, t), 5.0–5.2 (3H, m).

EXAMPLE 19

(E)-3,7,11-Trimethyl-6,10-dodecadien-1-ol

To 150 ml. of anhydrous diethyl ether there was added 1.9 g. of lithium aluminum hydride. To the mixture was dropwise added, under stirring and at 10° C., 11.9 g. of the carboxylic acid compound obtained in Example 3. The resulting mixture was then stirred at room temperature for 1 hour, and then 1 ml. of ethyl acetate and 1 ml. of water were added thereto. The mixture was subsequently washed with water and dried. The solvent was removed by evaporation and the resulting residual oil was purified by silica gel column chromatography to obtain 10.3 g. of the desired oily product.

Infrared Absorption Spectrum (cm$^{-1}$, neat): 3,640.
Mass Spectrum: 224 ($M^+$).
Elementary Analysis (calculated for C$_{15}$H$_{28}$O):

| | C | H |
|---|---|---|
| Calculated (%) | 80.29 | 12.58 |
| Found (%) | 80.14 | 12.51 |

NMR Spectrum ($\delta$, CDCl$_3$): 0.99 (3H, d), 1.2–1.5 (5H, m), 1.6 (6H, s), 1.72 (3H, s), 1.9–2.2 (7H, m), 3.6 (2H, d), 5.0–5.2 (2H, m).

EXAMPLES 20-32

In Examples 20 through 32, a variety of compounds according to the invention were prepared in the same manner as described in Examples 17 through 19. The compounds and the resulting data are set forth in Table 3.

TABLE 3

$$H+CH_2-\underset{CH_3}{\underset{|}{C}}=CH-CH_2\overline{)_n}CH_2-\underset{CH_3}{\underset{|}{CH}}-CH_2-CH_2OR_1 \quad (III)$$

| Ex. | n | $R_1$ | Molecular Formula Property | Analysis: Calculated (%) / Found (%) C | Analysis: Calculated (%) / Found (%) H | Mass Spectrum ($M^+$) | NMR Spectrum ($\delta$, $CDCl_3$) |
|---|---|---|---|---|---|---|---|
| 20 | 1 | H | $C_{10}H_{20}O$ Oil | 76.86 / 76.80 | 12.90 / 12.96 | 156 | 0.99 (3H, d), 1.2~1.5 (5H, m), 1.6 (3H, s), 1.72 (3H, s), 1.9~2.2 (3H, m), 3.6 (2H, t), 5.0~5.2 (1H, m) |
| 21 | 1 | $CH_3CO-$ | $C_{12}H_{22}O_2$ Oil | 72.68 / 72.55 | 11.18 / 11.20 | 198 | 0.99 (3H, d), 1.2~1.5 (5H, m), 1.6 (3H, s), 1.72 (3H, s), 1.9~2.2 (2H, m), 2.0 (3H, s), 4.2 (2H, t), 5.0~5.2 (1H, m) |
| 22 | 1 | $CH_3CH_2CO-$ | $C_{13}H_{24}O_2$ Oil | 73.53 / 73.45 | 11.39 / 11.34 | 212 | 0.99 (3H, d), 1.1 (3H, t), 1.2~1.5 (5H, m), 1.6 (3H, s), 1.72 (3H, s), 1.9~2.2 (2H, m), 2.2 (2H, q), 4.2 (2H, t), 5.0~5.2 (1H, m) |
| 23 | 1 | $CH_3CH_2CH_2-CO-$ | $C_{14}H_{26}O_2$ Oil | 74.21 / 76.64 | 11.50 / 11.35 | 226 | 0.9~1.1 (5H, m), 0.99 (3H, d), 1.2~1.5 (5H, m), 1.6 (3H, s), 1.72 (3H, s), 1.9~2.2 (2H, m), 2.2 (2H, t), 4.2 (2H, t), 5.0~5.2 (1H, m) |
| 24 | 2 | $CH_3CO-$ | $C_{17}H_{30}O_2$ Oil | 76.64 / 76.70 | 11.35 / 11.22 | 266 | 0.99 (3H, d), 1.2~1.5 (5H, m), 1.6 (6H, s), 1.72 (3H, s), 1.9~2.2 (6H, m), 2.0 (3H, s), 4.2 (2H, t), 5.0~5.2 (2H, m) |
| 25 | 2 | $CH_3CH_2CO-$ | $C_{18}H_{32}O_2$ Oil | 77.09 / 77.12 | 11.50 / 11.41 | 280 | 0.99 (3H, d), 1.1 (3H, t), 1.2~1.5 (5H, m), 1.6 (6H, s), 1.72 (3H, s), 1.9~2.2 (6H, m), 2.2 (2H, q), 4.2 (2H, t), 5.0~5.2 (2H, m) |
| 26 | 2 | $CH_3CH_2CH_2-CO-$ | $C_{19}H_{34}O_2$ Oil | 77.49 / 77.55 | 11.65 / 11.59 | 294 | 0.9~1.1 (5H, m), 0.99 (3H, d), 1.2~1.5 (5H, m), 1.6 (6H, s), 1.72 (3H, s), 1.9~2.2 (6H, m), 2.2 (2H, t), 4.2 (2H, t), 5.0~5.2 (2H, m) |
| 27 | 3 | $CH_3CH_2CO-$ | $C_{23}H_{40}O_2$ Oil | 79.25 / 79.08 | 11.57 / 11.62 | 348 | 0.99 (3H, d), 1.1 (3H, t), 1.2~1.5 (5H, m), 1.6 (9H, s), 1.72 (3H, s), 1.9~2.2 (10H, m), 2.2 (2H, q), 4.2 (2H, t), 5.0~5.2 (3H, m) |
| 28 | 3 | $CH_3CH_2CH_2-CO-$ | $C_{24}H_{42}O_2$ Oil | 79.50 / 79.39 | 11.68 / 11.54 | 362 | 0.9~1.1 (5H, m), 0.99 (3H, d), 1.2~1.5 (5H, m), 1.6 (9H, s), 1.72 (3H, s), 1.9~2.2 (10H, m), 2.2 (2H, t), 4.2 (2H, t), 5.0~5.2 (3H, m) |
| 29 | 4 | H | $C_{25}H_{44}O$ Oil | 83.26 / 83.08 | 12.30 / 12.18 | 360 | 0.99 (3H, d), 1.2~1.5 (5H, m), 1.6 (12H, s), 1.72 (3H, s), 1.9~2.2 (15H, m), 3.6 (2H, t), 5.0~5.2 (4H, m) |
| 30 | 4 | $CH_3CO-$ | $C_{27}H_{46}O_2$ Oil | 80.54 / 80.38 | 11.52 / 11.40 | 402 | 0.99 (3H, d), 1.2~1.5 (5H, m), 1.6 (12H, s), 1.72 (3H, s), 1.9~2.2 (14H, m), 2.0 (3H, s), 4.2 (2H, t), 5.0~5.2 (4H, m) |
| 31 | 4 | $CH_3CH_2CO-$ | $C_{28}H_{48}O_2$ Oil | 80.71 / 80.62 | 11.61 / 11.48 | 416 | 0.99 (3H, d), 1.1 (3H, t), 1.2~1.5 (5H, m), 1.6 (12H, s), 1.72 (3H, s), 1.9~2.2 (15H, m), 2.2 (2H, q), 4.2 (2H, t), 5.0~5.2 (4H, m) |

TABLE 3-continued

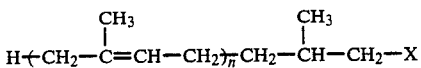

(III)

| Ex. | n | $R_1$ | Molecular Formula Property | Analysis: Calculated (%) Found (%) C | H | Mass Spectrum (M+) | NMR Spectrum ($\delta$, CDCl$_3$) |
|---|---|---|---|---|---|---|---|
| 32 | 4 | CH$_3$CH$_2$CH$_2$—CO— | C$_{29}$H$_{50}$O$_2$ | 80.87 / 80.99 | 11.70 / 11.58 | 430 | 0.9~1.1 (5H, m), 0.99 (3H, d), 1.2~1.5 (5H, m), 1.6 (12H, s), 1.72 (3H, s), 1.9~2.2 (14H, m), 2.2 (2H, t), 4.2 (2H, t), 5.0~5.2 (4H, m) |

EXAMPLE 33

| Preparation of tablets | |
|---|---|
| Product obtained in Example 1 | 50 g. |
| Silicic anhydride | 30 g. |
| Crystalline cellulose | 50 g. |
| Corn starch | 36 g. |
| Hydroxypropylcellulose | 10 g. |
| Calcium stearate | 4 g. |

This composition was processed in the conventional manner to obtain tablets (180 mg. per one tablet).

EXAMPLE 34

| Preparation of hard gelatin capsules | |
|---|---|
| Product obtained in Example 2 | 50 g. |
| Silicic anhydride | 35 g. |
| Silicic anhydride, hydrated | 5 g. |
| Crystalline cellulose | 50 g. |
| Hydroxypropylcellulose | 6 g. |
| Corn starch | 49 g. |
| Talc | 5 g. |

This composition was granulated in the conventional manner and charged into gelatin hard capsules (No. 3); 200 mg. per one capsule.

EXAMPLE 35

| Preparation of tablets | |
|---|---|
| Product obtained or Example 17 | 50 g. |
| Silicic anhydride | 30 g. |
| Crystalline cellulose | 50 g. |
| Corn starch | 36 g. |
| Hydroxypropylcellulose | 10 g. |
| Calcium stearate | 4 g. |

This composition was processes in the conventional manner to obtain tablets (180 mg. per one tablet).

EXAMPLE 36

| Preparation of hard gelatin capsules | |
|---|---|
| Product obtained in Example 18 | 50 g. |
| Silicic anhydride | 35 g. |
| Silicic anhydride, hydrated | 5 g. |
| Crystalline cellulose | 50 g. |
| Hydroxypropylcellulose | 6 g. |
| Corn starch | 49 g. |
| Talc | 5 g. |

This composition was granulated in the conventional manner and charged into gelatin hard capsules (No. 3); 200 mg. per one capsule.

The embodiments of the invention in which an exclusive property or privilege is claimed are defined as follows:

1. A compound having the formula:

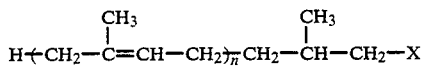

wherein X is —COOR$_1$ or —CH$_2$OR$_2$, in which R$_1$ is hydrogen or alkyl having one to four carbon atoms and R$_2$ is hydrogen or aliphatic acyl having one to four carbon atoms; and n is an integer of one to four.

2. A compound as claimed in claim 1, in which X is —COOR$_1$.

3. A compound as claimed in claim 1, in which X is —CH$_2$OR$_2$.

4. A compound as claimed in claim 1 which is (E, E)-3,7,11,15-tetramethyl-6,10,14-hexadecatrienoic acid.

5. A compound as claimed in claim 1 which is ethyl (E, E)-3,7,11,15-tetramethyl-6,10,14-hexadecatrienoate.

6. A compound as claimed in claim 1 which is (E, E)-3,7,11,15-tetramethyl-6,10,14-hexadecatrien-1-ol.

7. A compound as claimed in claim 1 which is (E, E)-3,7,11,15-tetramethyl-6,10,14-hexadecatrienyl acetate.

8. A pharmacological composition for the treatment of liver hepatitis comprising a therapeutically effective amount of a compound having the formula:

wherein X is —COOR$_1$ or —CH$_2$OR$_2$, in which R$_1$ is hydrogen or a lower alkyl group and R$_2$ is hydrogen or aliphatic acyl having one to four carbon atoms; and n is an integer of one to four, in combination with a pharmacological carrier.

9. A composition as claimed in claim 8, in which X is —COOR$_1$.

10. A composition as claimed in claim 8, in which X is —CH$_2$OR$_2$.

11. A composition as claimed in claim 8 which said compound is (E, E)-3,7,11,15-tetramethyl-6,10,14-hexadecatrienoic acid.

12. A composition as claimed in claim 8 which said compound is ethyl (E, E)-3,7,11,15-tetramethyl-6,10,14-hexadecatrienoate.

13. A composition as claimed in claim 8 which said compound is (E, E)-3,7,11,15-tetramethyl-6,10,14-hexadecatrien-1-ol.

14. A composition as claimed in claim 8 which said compound is (E, E)-3,7,11,15-tetramethyl-6,10,14-hexadecatrienyl acetate.

* * * * *